(12) United States Patent
Ingber et al.

(10) Patent No.: US 8,931,490 B2
(45) Date of Patent: Jan. 13, 2015

(54) SYSTEMS AND METHODS FOR NANOMAGNETIC ACTUATION OF MOLECULAR CELL SIGNALING

(75) Inventors: Donald E. Ingber, Boston, MA (US); Robert J. Mannix, Boston, MA (US); Sanjay Kumar, Moraga, CA (US)

(73) Assignee: Children's Medical Center Corporation, Boston, MA (US)

(*) Notice: Subject to any disclaimer, the term of this patent is extended or adjusted under 35 U.S.C. 154(b) by 1277 days.

(21) Appl. No.: 12/595,306

(22) PCT Filed: Apr. 9, 2008

(86) PCT No.: PCT/US2008/059738
§ 371 (c)(1),
(2), (4) Date: Apr. 5, 2010

(87) PCT Pub. No.: WO2008/156904
PCT Pub. Date: Dec. 24, 2008

(65) Prior Publication Data
US 2010/0203143 A1    Aug. 12, 2010

Related U.S. Application Data

(60) Provisional application No. 60/922,561, filed on Apr. 9, 2007.

(51) Int. Cl.
*A61B 19/00* (2006.01)
*A61K 9/16* (2006.01)
(Continued)

(52) U.S. Cl.
CPC ....... *A61K 41/0052* (2013.01); *A61K 47/48507* (2013.01); *A61N 2/00* (2013.01); *Y10S 977/904* (2013.01)

USPC ..... 128/899; 424/489; 435/173.1; 435/173.4; 435/173.8; 600/9; 600/12; 977/904

(58) Field of Classification Search
USPC ......... 128/897–899; 435/173.1, 173.4, 173.8; 977/904, 915; 600/9
See application file for complete search history.

(56) References Cited

U.S. PATENT DOCUMENTS 6,132,360 A    10/2000  Halpern
6,687,530 B2 *  2/2004  Dumoulin .................... 600/423
(Continued)

FOREIGN PATENT DOCUMENTS

WO    01/17611 A    3/2001
WO    2005/065282 A    7/2005
(Continued)

OTHER PUBLICATIONS

Alenghat, F.J. et al., IEEE Transactions on Magnetics, 40(4):2958-2960 (2004). "Magnetic Cellular Switches."
(Continued)

*Primary Examiner* — Charles A Marmor, II
*Assistant Examiner* — Thaddeus Cox
(74) *Attorney, Agent, or Firm* — Nixon Peabody LLP; David S. Resnick

(57) ABSTRACT

The present invention relates to signaling mechanisms that transduce magnetic inputs into physiological cellular outputs. More particularly, the present invention relates to systems and methods for non-invasively controlling cellular signaling functions and behaviors by harnessing receptor-mediated and intracellular molecular-mediated signal transduction using nanomagnetic cellular switches.

22 Claims, 5 Drawing Sheets

(51) Int. Cl.
*A61N 2/00* (2006.01)
*C12N 13/00* (2006.01)
*A61K 41/00* (2006.01)
*A61K 47/48* (2006.01)

(56) References Cited

U.S. PATENT DOCUMENTS

| | | | |
|---|---|---|---|
| 8,001,977 B2 * | 8/2011 | Seeney et al. | 128/899 |
| 2006/0286089 A1 * | 12/2006 | Berenson et al. | 424/131.1 |
| 2009/0169478 A1 * | 7/2009 | Leuschner et al. | 424/9.3 |
| 2011/0034753 A1 * | 2/2011 | Dobson et al. | 600/12 |

FOREIGN PATENT DOCUMENTS

| | | |
|---|---|---|
| WO | 2006/039675 A | 4/2006 |
| WO | 2006/138612 A | 12/2006 |

OTHER PUBLICATIONS

Neuberger, T. et al., Journal of Magnetism and Magnetic Materials, 293(1):483-496 (2005). "Superparamagnetic nanoparticles for biomedical applications: Possibilities and limitations of a new drug delivery system."

* cited by examiner

SYSTEMS AND METHODS FOR NANOMAGNETIC ACTUATION OF MOLECULAR CELL SIGNALING

This invention was made with U.S. government support under grant No. F32-NSO48669 awarded by the National Institutes of Health and grant No. N000140210780 awarded by the Defense Advanced Research Projects Agency. The U.S. Government has certain rights in the invention.

CROSS REFERENCE TO RELATED APPLICATIONS

The present application is a 35 U.S.C. §371 U.S. National Phase Entry of International Application No. PCT/US2008/059738 filed Apr. 9, 2008, which designates the U.S., and which claims the benefit of priority under 35 U.S.C. §119(e) of U.S. Provisional Patent Application Ser. No. 60/922,561 entitled filed Apr. 9, 2007, the contents of which are incorporated herein by reference in its entirety.

FIELD OF THE INVENTION

The present invention relates to signaling mechanisms that transduce magnetic inputs into physiological outputs in living cells. More particularly, the present invention relates to devices and methods for non-invasively controlling intracellular functions using nanomagnetic cellular switches.

BACKGROUND OF THE INVENTION

A fundamental principle of cell biology is that complex behaviors such as cell growth, differentiation, motility, and apoptosis are controlled by receptor-mediated signal transduction, which impacts gene expression, protein synthesis, and cell metabolism by triggering a series of molecular-mediated intracellular signaling cascades. Receptor-mediated signal transduction allows cells to convert one type of stimulus into a different type of stimulus, the receptor acting as the intermediary in carrying out the conversion. Such transduction is often triggered by the binding of chemical ligands, such as hormones, cytokines, and adhesive macromolecules to cell surface receptors and propagated by specific binding of different molecules inside the cell. Hence, conventional approaches to transduction-mediated cellular control have relied upon the use of these chemical cues.

Although living cells exhibit a capacity for signal detection and information processing far beyond that of man-made technologies, one of the major limitations in developing living cells as signal detectors has been the lack of a suitable control interface between cells and existing microtechnologies. But these natural chemical signals are not always well-suited in microtechnologies, however, such as medical devices, drug delivery systems, biocomputers, man-machine interfaces, and other techniques that incorporate living cells as system components. To be effective, cellular devices require actuation mechanisms that are much more robust, non-invasive, and relatively free of side effects. For efficacy, cellular devices also require actuation mechanisms that are easy to interface with physical inputs, rather than chemical inputs. Chemical cues are also distributed throughout the entire body when injected into patients, and thus they do not provide spatial control of their actions when used clinically.

A few highly specialized cell types, including neurons and myocytes, have been activated using electrical stimuli, and microelectrode arrays have been developed in attempts to influence the activity of these cells in microdevices and in patients. Most cells are not electrically active in this way, however, and switches activated by electrical signals have high power requirements, so this approach may not be generalized for cellular microsystems design. Medical microdevices that require electrical stimulation also often require indwelling wires or transcutaneous electrodes that can lead to medical complications, such as infection.

None of the current approaches provides for highly practical or portable devices that overcome the above deficiencies nor mechanisms to provide spatial control over chemical signaling behaviors in cells in vivo, and past approaches have fallen short in that no suitable cellular actuation mechanism exists that is more robust, non-invasive, and easy to interface with physical inputs. Likewise, prior attempts have not been successful in producing low-power actuation mechanisms to initiate cellular signaling. Magnetic systems offer this form of non-invasive control with minimal power requirements, and thus, there is a need for systems and methods for magnetic control technologies to rapidly and reversibly control a wide range of cellular signal transduction pathways that would overcome these limitations, such as a magnetic actuation mechanism that is broadly applicable to a vast array of cell types and receptor systems useful, for example, for magnetodynamic therapy.

SUMMARY OF THE INVENTION

Living cells demonstrate a capacity for signal detection and information processing far beyond that of man-made technologies. Integrating cells into biosensors, diagnostic devices, and therapeutic approaches extends the efficacy of conventional signaling and processing equipment. For example, mammalian cells may be employed as signal processing elements within microelectronic devices, as interfaces between man and machine, and as sensors for human biopathogens. Nanomagnetic interfaces that link to physiological cellular signal transduction mechanisms in accordance with the present invention provide this type of functional control and open an entirely new and previously unrecognized mechanism to interface living and physical systems. Specifically, the systems and methods of the present invention provide a bio-magnetic interface employing nanomagnetic cellular switches that permit non-invasive actuation of specific cellular behaviors with high fidelity.

Cells often rely upon their surface receptors to sense their environment. Many receptors interact with specific ligand molecules, triggering a cascade of intracellular biochemical events. These biochemical events then lead to cell behaviors, such as cell growth, differentiation, apoptosis, and movement; the secretion of hormones; wound healing; heart, skeletal and smooth muscle contractility; nerve impulses in the central and peripheral nervous system; mounting of an immune response and destruction of pathogens; and the like. In numerous classes of ligand/receptor interactions, divalent or multivalent ligand binding initiates receptor dimerization or clustering (oligomerization), which is required for activation of intracellular signaling events. The systems and methods of the present invention provide for the activation cell surface of receptors by attaching nanometer-sized magnetic particles to ligands for target receptors. When these magnetic particles that are on the same scale as individual molecules are bound to the target receptor and then magnetized, the magnetic particle-bound ligands attract each other and force the linked receptors to dimerize or cluster, and hence to activate. This clustering-induced activation triggers the desired biochemical events inside the cell. In this fashion, the present invention employs magnetic forces to physically promote molecular receptor clustering and thereby mimic oligomerization-dependent activation mechanisms that are induced by binding of cell surface receptors to their natural chemical ligands.

Intracellular signal transduction is also mediated by binding or clustering of specific intracellular molecules in the cytoplasm, nucleus or other intracellular organelles, such as endoplasmic reticulum, sarcoplasmic reticulum and mitochondria, that only trigger downstream signaling and biochemical responses when two or more molecules come in close physical apposition. These molecular binding or aggregation events are normally mediated by post-translational modifications of one or more of the interaction molecules, such as protein phosphorylation, myristoylation or binding of calcium, lipids, cAMP or nucleotide di- or tri-phosphates, G protein and inositol lipid signaling, that are induced by upstream signaling cascades. Thus, in one embodiment of the invention, the systems and methods of the present invention provide for the activation of intracellular biochemical responses by introducing magnetic particles into the cytoplasm, nucleus or other intracellular compartments of the cell that bind to two or more molecules. When bound to the target molecules and then magnetized, the magnetic particle-bound molecules attract each other and force the molecules to dimerize or cluster. This magnetic force-induced molecular aggregate triggers the desired biochemical events inside the cell, thereby mimicking the activation normally induced by chemical signal-induced post-translational modification of the molecule. In this fashion, the present invention employs magnetic forces to physically promote molecular aggregation and thereby mimic oligomerization-dependent activation mechanisms that are induced by specific binding of different molecules through chemical modifications that mediate signal transduction.

In another embodiment of the invention, the system of the present invention includes a high fidelity nanomagnetic cellular switch that can be chemically tuned, magnetically actuated, and reversibly switched back to its "off" state, either once or repeatedly. This control mechanism may be integrated as part of a microfluidic or biological system. A nanomagnetic cellular switch in accordance with the present invention may also serve as a non-invasive control element within an integrated microdevice for sensing functionally relevant signals, such as pathogens, and the like. In an additional aspect of the present invention, the systems and methods include nanomagnetic particles linked to specific cell surface receptors or intracellular molecules that generate intracellular chemical signals when magnetically stressed, or when cell shape is distorted. These signals then activate a bistable switch with a tunable threshold. Once "flipped," this toggle switch, for example, triggers the production of enzymes that produce and further amplify production of a readout signal that is detectable by optical sensors. This switch may be further enhanced by incorporating auto-catalytic loops to provide additional signal amplification. The switches also may be linked to various types of readouts, such as pigment, chemical, electronic, and the like, as well as to micro sensors.

Moreover, the present invention provides for the manipulation of receptor signaling pathways to magnetically control cell structure and function. These robust magnetically-actuated cellular switches can be removed from a laboratory environment and integrated with other microtechnologies and nanotechnologies and used in biodefense applications, biotechnology applications, and clinical applications. This system may be used clinically by injecting magnetic particles coated with ligands into the body and applying magnetic fields across a distances, such as transdermally or via endoscopy across the lining of the internal organs of the body.

The system of the present invention also provides for high-density, multiplexed magnetic field gradient concentrators using laser-etching of magnetizable substrates that may be used in vitro or in vivo. This multiplexed system is then used to magnetically actuate switches that control cellular behaviors, such as apoptosis, and the like.

In addition, the systems and methods of the present invention employ a genetically engineered signal processing module, such as one based on a bistable genetic switch, to provide a generic mechanism for amplifying magnetically-induced signals in living cells as well as a tunable detection threshold. This switch may be used to magnetically actuate or tune expression of specific gene products encoded by genes that are under control of this switch, such as the production of insulin, erythropoietin, GM-CSF, and the like. Various nanomagnetic beads and magnet architectures may be used to optimize the efficiency of magnetic actuation and to interface these materials with microfluidic, micro-optical, and microelectronic sensing systems. Cells containing these genetic engineered control systems may be implanted in the body and thereby used as magnetically controlled drug manufacturing devices or biomolecular detectors and sensors using this non-invasive magnetic control system.

BRIEF DESCRIPTION OF THE DRAWINGS

The accompanying drawings illustrate an embodiment of the invention and depict the above-mentioned and other features of this invention and the manner of attaining them.

FIG. 1A: Changes in intracellular calcium concentration ($[Ca^{2+}]i$) in RBL-2H3 mast cells in which surface membrane FcERI receptors were preloaded with anti-DNP IgE antibodies. Changes in calcium concentration were measured using Fura-2 ratiometric imaging and induced by adding soluble multivalent DNP-HSA (100 ng/ml) (○) or soluble monovalent DNP-Lys (100 μg ml$^{-1}$) (●). FIG. 1B: Signaling induced by adding magnetic nanobeads (30 nm diameter) coated with 30 (○), 3 (Δ) or 1 (■) DNP per bead. Arrows indicate the time at which the soluble DNP (a) and DNP-coated magnetic nanobeads were added.

FIG. 3. Nanomagnetic control of receptor signal transduction.

FIG. 4A: Magnetic control over changes in intracellular calcium ($A[Ca^{2+}]i$) by applying five electromagnetic pulses of 1-min duration (0.1 Amp, 0.3 Amp, 1 Amp, 1 Amp and 1 Amp, arrows) separated by 1-min rest periods (mean±standard error). FIG. 4B: Low (top; scale bar, 100 µm) and high (bottom; scale bar, 10 µm) magnification views of pseudocoloured microfluorimetric images showing repeated on- and off-switching of calcium signaling in groups of cells (top) and individual cells (bottom) that precisely coincide with activation and deactivation of the magnetic field, respectively. FIG. 4C Effect of a more rapid cyclical magnetic stimulation regimen (40 s on, 20 s off; 1 Amp) on intracellular calcium signaling. FIG. 4D: $[Ca^{2+}]i$ changes measured in individual cells from the study shown in panel C. Arrows in panels C and D indicate the start of magnetic pulses.

DETAILED DESCRIPTION OF THE INVENTION

Figure 1:
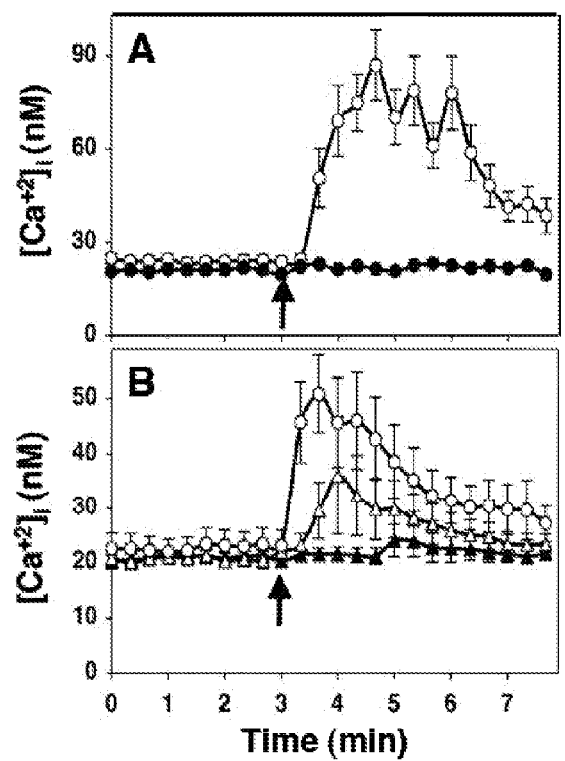
FIG. 1. Activation of intracellular calcium signaling by crosslinking surface-bound IgE antibodies.

It should be understood that this invention is not limited to the particular methodology, protocols, and reagents, and the like described herein, and as such, the embodiments described may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

The present invention provides systems and methods whereby binding magnetic nanoparticles to molecules on the surface, in the cytoplasm, nucleus or other intracellular compartments of living cells allows for manipulation and control of cell functions via an applied magnetic field. These techniques are not only an important investigative tool, but they may be used to actively control cellular functions and processes in a wide variety of biological and clinical applications never before possible. The ability to manipulate and remotely control specific cellular biochemical activities in vitro and in vivo provides clinicians and scientists with a powerful tool for investigating cell function and molecular signaling pathways. For example, the systems and methods of the present invention allow biologists to probe the mechanisms governing ion channel activity, to elucidate pathways that lead to activities, such as growth, differentiation, motility, contractility, apoptosis, gene transcription, and the production of proteins and stress responses. These systems and methods may be used to actuate or control cells within devices, such as biodetectors or medical devices and to develop new treatments for medical conditions, including cancer, heart arrhythmias, hormonal deficiencies, and inflammatory diseases.

A major advantage is that nanomagnetic actuation allows "action at a distance" with precise spatial control. The magnetic field may be coupled to a particle to actuate a process within a target cell regardless of whether there are intervening structures, such as tissue. This actuation process presents distinct advantages for in vivo applications. Additionally, control parameters may be varied dynamically simply by varying the strength of the applied field over time. Another advantage is the precision afforded by the technique that can be used, for example, to target, to manipulate, and to activate individual ion channels or surface receptors on specific cells within a culture or at specific sites within tissues in a living animal or patient.

Nanomagnetic actuation is useful in several areas of biology and biomedical science including investigations of cell mechanical properties, mechanosensitive ion channel signaling pathways, targeted activation of specific membrane receptors or intracellular signaling pathways, construction of "biochips", non-invasive pacing of contractile or nerve cells, non-invasive control of protein or hormone production, and mechanical conditioning of cells for regenerative medicine applications.

More specifically, the present invention provides systems and methods for rapidly and reversibly controlling transmembrane or intracellular signal transduction pathways using a nanomagnetic actuation mechanism that is broadly applicable to a variety of cell types and cellular receptor systems. Many complex cell behaviors are triggered by chemical ligands that bind to membrane receptors and alter intracellular signal transduction. Biosensors, medical devices, and other microtechnologies that incorporate living cells as system components, require actuation mechanisms that are more rapid, robust, non-invasive and easily integrated with solid-state interfaces than are chemical ligands. The present invention provides systems and methods for a magnetic nanotechnology that activates a biochemical signaling mechanism normally switched on by binding of multivalent chemical ligands. For example, superparamagnetic 30-nm beads, coated with monovalent ligands and bound to transmembrane receptors, are magnetized when exposed to magnetic fields, and aggregate owing to bead-bead magnetic attraction in the plane of the membrane. Associated clustering of the bound receptors acts as a nanomagnetic cellular switch that directly transduces magnetic inputs into physiological cellular outputs with rapid system responsiveness and non-invasive dynamic control. This approach presents a novel actuator mechanism for cell-based microtechnologies and man-machine interfaces. Similar approaches can be used with magnetic nanoparticles introduced into the cytoplasm of cells that aggregate and thereby trigger specific chemical activities, such as gene transcription, when magnetic fields are applied.

Currently, microdevices containing microelectrode arrays have been developed to influence the activity of neurons and myocytes with electrical stimuli (Fromherz et al., 252 Science, 1290-93 (1991); Young & Chen, 27 Biomats. 3361-67 (2006)), but this approach cannot be used in the control of microsystems containing non-excitable cells. Therefore, an alternative to electrical actuation would be highly desirable, particularly one that is more robust, chemically specific and has lower power requirements. The present invention provides systems and methods to rapidly and reversibly control a much wider range of transmembrane signal transduction pathways using a nanoscale magnetic actuation mechanism, which is an approach that is broadly applicable to a vast array of cell types and receptor systems. In a system and method of the present invention, magnetic forces are used in combination with receptor-bound magnetic nanobeads to physically promote receptor clustering and thereby mimic oligomerization-dependent activation mechanisms, which are induced by binding of natural multivalent chemical ligands to cell surface receptors. Similar approaches can be used with magnetic nanoparticles introduced into the cytoplasm or nucleus of cells that aggregate and thereby trigger specific chemical activities, such as gene transcription, when magnetic fields are applied.

The requirement for receptor clustering for activation of signal transduction is a hallmark of many types of receptors, including ones that bind immunogens (Bromley et al., 19 Annu. Rev. Immunol., 375-96 (2001)), cytokines (Schreiber et al., 258 J. Biol. Chem., 846-53 (1983)), neurotransmitters (Kim et al., 17 Neuron, 103-13 (1996)), and metabolites (Rothberg et al., 111 J. Cell Biol., 2931-38 (1990)). The novel magnetic nanotechnology provided by the present invention, which can make use of any type of surface membrane receptor that requires a multivalent ligand for signal activation, opens many new avenues to control cellular metabolisms using non-invasive magnetic control. For example, because this magnetic cellular switch permits the transduction of magnetic inputs into biological signals with precise spatiotemporal control, the magnetic cellular switch represents a valuable tool with which to control the behavior of living cellular components within the microtechnologies and biochips that are beginning to be used in biomedical devices, sensors, drug delivery systems, and other types of man-machine interfaces. For example, nanomagnetic cellular switches enable non-invasive magnetic control of intracellular functions, including receptor signal transduction, gene transcription, protein synthesis, hormone secretion, initiation of the cellular suicide response, and the like.

The systems of the present invention may include one or more of the following devices, components, or concepts: (a) micro- or nano-magnetic cellular switches that generate receptor signals detectable by optical methods or other non-invasive detectors; (b) recombinant gene modules that enable non-invasive magnetic control of production of specific gene products; (c) an electromagnet or permanent magnet to apply magnetic fields, (d) high-density, multiplexed magnetic field gradient architecture for manipulation and control of nanomagnetic particles and cells; and (e) high fidelity, nanomagnetic cellular switches that control signal transduction and cell behavior.

The present invention also offers systems and methods with the ability to add similar functionality to other multifunctional imaging nanotechnologies that are designed to control spatial assembly of cells (Tanase et al., 5 Lab. Chip, 598-605 (2005)) or to simultaneously localize diseased tissues (for example, tumors), or to release therapeutics and monitor response to therapy (Koo et al., 58 Adv. Drug Deliv. Rev., 1556-77 (2006)). Ligand-conjugated superparamagnetic nanoparticles have been approved for clinical use as contrast agents in magnetic resonance imaging (Bulte & Kraitchman, 17 NMR Biomed. 484-99 (2004)). Thus, a cellular magnetic switch in accordance with the present invention may be used in conjunction with magnetic fields applied across the skin or the lining of internal organs to control cellular functions in vivo, including immunological responses and cancer cell viability. Other technologies may see their scope and impact extended dramatically with the use of magnetic control elements in accordance with the present invention that are capable of actuating specific transmembrane receptor signaling mechanisms at precise times and locations. By providing a non-invasive method to convert magnetic inputs into receptor-specific biological outputs, the nanotechnology-based receptor actuation mechanism of the present invention represents an important step toward this form of magnetic cellular control.

The proof-of-principle for the approach of the present invention was demonstrated by manipulating cellular behavior by using superparamagnetic nanoparticles and a magnetic field to cluster the IgE receptors on the surface of living mast cells. Mast cells perform immune surveillance in living tissues by expressing plasma membrane FcεRI receptors that engage Fc portions of single IgE molecules. When they are not activated, mast cells present these receptor-antibody complexes individually (unclustered) on their surface membrane for extended periods of time. Sutton & Gould, 366 Nature, 421-28 (1993). When multivalent antigens (immunogens) bind to the exposed variable portion of these bound IgE molecules, they induce FcεRI receptor oligomerization. Receptor clustering triggers an intracellular signaling response characterized by a rapid rise in cytosolic calcium due to influx from the extracellular space and release from intracellular stores (Lu-Kuo et al., 274 J. Biol. Chem. 5791-96 (1999)); this chemical messenger, in turn, triggers vesicle degranulation and histamine release, which initiate the local inflammatory response. Segal et al., 74 Proc. Natl. Acad. Sci. USA, 2993-97 (1977).

As an initial step in determining whether the mast cell mechanism could be harnessed using a magnetic nanotechnology, RBL-2H3 mast cells were preincubated with IgE directed against the dinitrophenyl (DNP) antigen so that these 'primed' cells would present these antibodies on their surface bound to FcεRI receptors. Treatment of cells with a bolus of soluble horse serum albumin derivatized with multiple DNP moieties (DNP-HSA) resulted in a transient threefold increase in mean cytosolic calcium within 1 min-2 min of addition (FIG. 1A), consistent with previous reports in these cells, which confirm that multivalent ligands that induce FcεRI receptor clustering trigger intracellular signaling in these cells (Oka et al., 286 Am. J. Physiol. Cell Physiol. C256-63 (2004)). In contrast, addition of soluble monovalent DNP-lysine (DNP-Lys) failed to activate a calcium signaling response (FIG. 1A). Moreover, when DNP-HSA was added to cells pre-treated with excess DNP-Lys, calcium signaling was completely inhibited (FIG. 5), confirming that soluble monovalent ligands bind to these receptors. Thus, multivalency, and not ligation alone, is required for FcεRI receptor activation.

Figure 2:
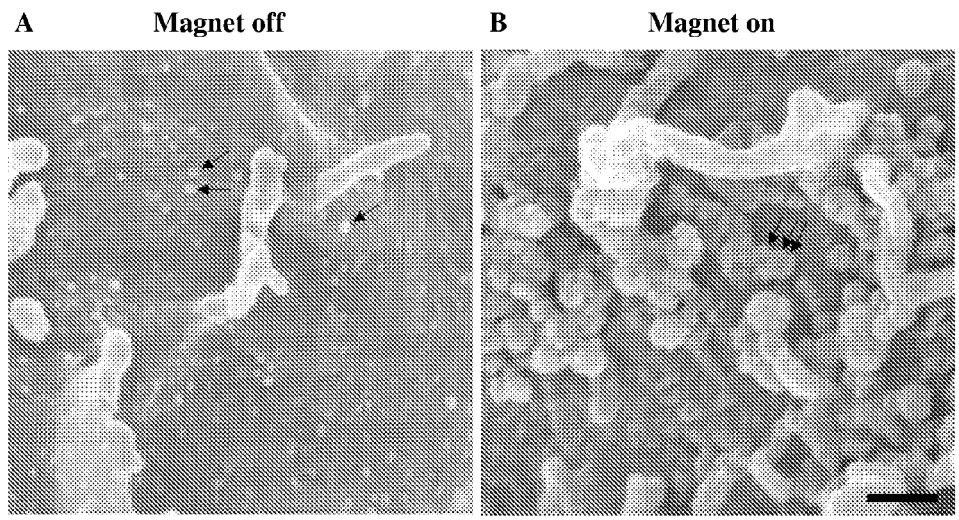
FIG. 2. Visualization of magnetically-induced clustering of single DNP-coated nanobeads with an electron microscope. Mast cells were pre-treated with anti-DNP IgE overnight to load the FcεRI receptors, incubated with monovalent DNP beads (30 nm) for 3h, washed free of unattached beads, fixed before (A, magnet off) or after (B, magnet on) application of electromagnetic force (1 Amp) for 2 min, and imaged with scanning electron microscopy. Arrows in (A) indicate individual bound nanobeads distributed over the cell surface in the absence of the electromagnetic force, which cluster as large aggregates as shown in (B) when the magnetic switch is activated (scale bar: 300 nm).

Superparamagnetic nanoparticles (30 nm in diameter) covalently conjugated to approximately 30 DNP-Lys ligands per bead were then added to cells pre-treated with anti-DNP IgE. Binding of these multivalent nanobeads to cell surface IgE-FcεRI receptor complexes resulted in activation of a similar threefold increase in intracellular calcium, but with even faster dynamics (compare FIG. 1B and FIG. 1A). Importantly, when the antigen density of each nanobead was reduced to approximately three DNP ligands per bead, calcium signaling was significantly suppressed, and when it was reduced to one DNP per bead (monovalency), there was no detectable response (FIG. 1B). Beads coated with one DNP per bead did, however, bind to cell surface receptors, as confirmed by scanning electron microscopy (SEM), which demonstrated isolated 30-nm beads distributed evenly across the plasma membrane in the absence of an applied magnetic field (FIG. 2). Quantitative examination of 20 SEM images of different cells confirmed that more than 95% of control cells displayed only well-scattered, single attached beads. Thus, binding of magnetic nanobeads coated with monovalent DNP ligands to FcεRI receptors does not activate intracellular calcium signaling, because they fail to cluster and crosslink neighboring receptors.

Figure 3A:
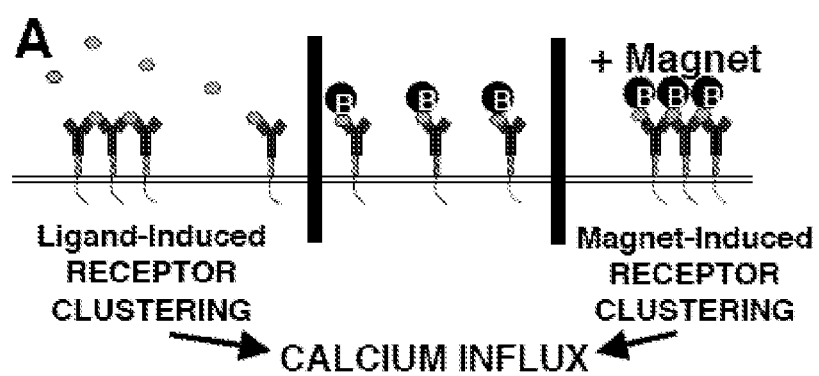
FIG. 3A: The biochemical mechanism that stimulates downstream signaling (left) involves the binding of multivalent ligands (small hexagons) that induce oligomerization of individual IgE/FcεRI receptor complexes. In the magnetic switch, monovalent ligand-coated magnetic nanobeads (dark grey circles), similar in size to individual FcεRI receptors, bind individual IgE/FcεRI receptor complexes without inducing receptor clustering (center). Applying a magnetic field that magnetizes the beads and pulls them into tight clusters (right) rapidly switches on receptor oligomerization and calcium signaling.
Figure 3B:
FIG. 3B, The pseudocolored microfluorimetric image shows the local induction of calcium signaling (yellow, appears light gray in FIG. 3B) in cells near the tip of the electromagnet within 20 s of the field (1 Amp) being applied. Scale bar, 50 µm.
Figure 3C:
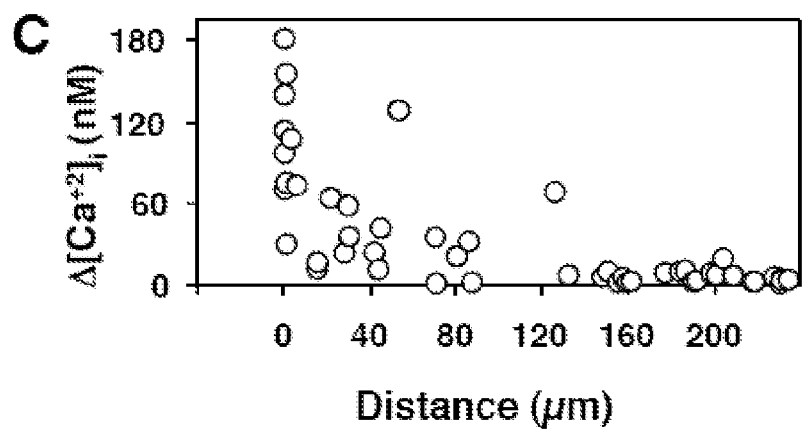
FIG. 3C: Quantification of peak changes in intracellular calcium relative to time 0 ($\Delta[Ca^{2+}]i$) measured within individual cells during a 1-min pulse of applied magnetic force (1 Amp) as a function of the distance of the tip from the cell surface.
Figure 4:
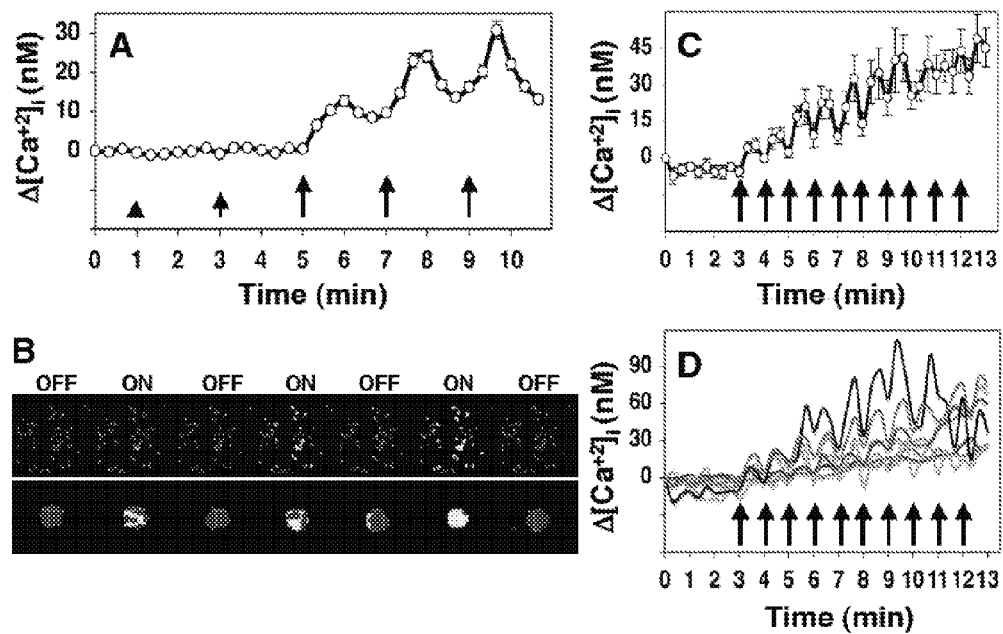
FIG. 4. Dynamic responsiveness and reversibility of magnetically induced receptor signaling. Mast cells were pretreated with anti-DNP IgE and monovalent DNP-coated nanobeads and subjected to time-dependent magnetic forces.

Based on these findings, it was reasoned that a magnetic cellular switch could be created to control calcium signaling in these cells by applying magnetic fields to magnetize the bound superparamagnetic nanobeads, and thus physically induce cohesion and aggregation of nanobead-receptor complexes on the cell membrane (FIG. 3A). To accomplish this, cells were pretreated with IgE overnight, incubated with superparamagnetic nanobeads (1 DNP/bead) for 3 h, washed free of unbound beads, and then exposed to magnetic fields applied using an electromagnetic needle. See Matthews et al., 85 Appl. Phys. Lett. 2968-70 (2004); Matthews et al., 119 J. Cell Sci. 508-18 (2006). The tip of the needle was placed near (<300 μm) the surface of cultured cells, and electrical pulses of increasing current (0.1 Amp, 0.3 Amp, and 1 Amp) were applied to the electromagnet for 1 min separated by 1 min rest periods. Microfluorimetry revealed that a rapid rise in intracellular calcium was produced by the highest field strength (FIG. 3B and FIG. 4A). Calcium levels rose more than 12 nM in some cells located within ~10 μm of the tip of the needle, and there was a sharp dependence of this calcium signaling response on the proximity of the cell to the needle tip (FIG. 3C). This spatial response closely mirrors the magnetic field strength, which also drops steeply as a function of distance from the magnet. See Matthews et al., 313 Biochem. Biophys. Res. Commun. 758-64 (2004).

Figure 5:
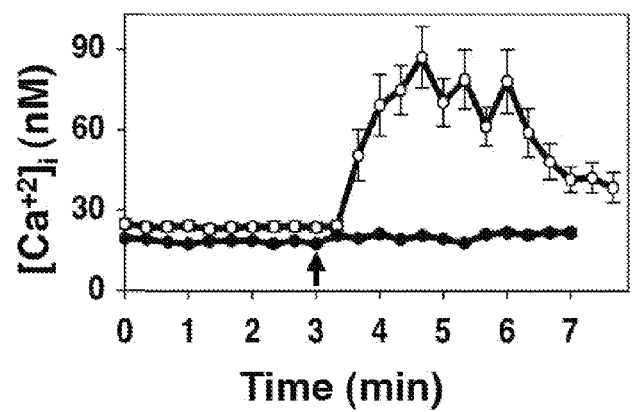
FIG. 5. Specificity of receptor-mediated calcium signaling. The induction of calcium signaling induced by addition of soluble multivalent DNP-HAS (100 ng/ml) (○) as shown in FIG. 1A can be completely inhibited by adding excess soluble monovalent DNP-Lys (100 m/ml) to cells expressing IgE/Fc RI receptor complexes on their surface prior to DNP-HAS addition (●). Arrow indicates time of DNP-HSA addition; data represent mean±standard error.
Figure 7:
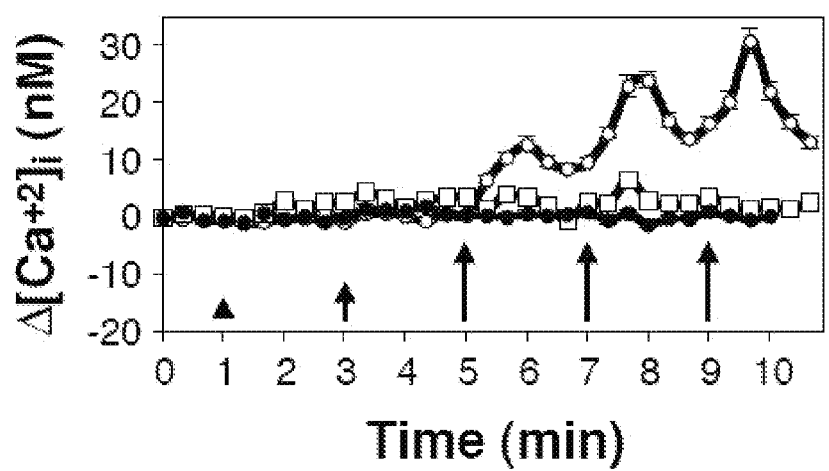
FIG. 7. Priming of FcεRI receptors with anti-DNP IgE antibodies is required for signaling. Cells require anti-DNP IgE antibodies bound to their FcεRI receptors to activate calcium signaling following addition of DNP-coated magnetic nanobeads and application of increasing electromagnetic fields (0.1, 0.3, and 1 Amp) separated by 1 min rest periods. The signaling induced by addition of monovalent DNP-nanobeads to cells pretreated overnight with anti-DNP IgE (○) did not occur in cells that were not pretreated with IgE (●). Similar negative results were obtained with cells treated with IgE and nanobeads coated with L-lysine rather than DNP-lysine (□).

Importantly, SEM analysis confirmed that the receptor-bound nanobeads that appeared evenly distributed across the surface membrane of control cells aggregated into large closely packed clusters on the cell surface when the highest magnetic field was applied (FIG. 2B). Quantitative analysis of nearest-neighbor distances between 300 bead-bead pairs in five SEM images of different cells revealed that the separation distance was less than one bead diameter (27.7 nm±1.7 nm) before application of the magnetic field. Importantly, finite-element modeling of the forces exerted on individual beads and between neighboring beads under these conditions confirmed that at the microneedle-bead separation distance used in this study (>30 μm), the magnitude of the tangential attractive force between neighboring beads was more than an order of magnitude larger than the normal (tensional) force exerted on each nanobead (FIG. 5). Moreover, the magnitude of the normal force on the beads was less than $10^{-17}$ N, which is many orders of magnitude smaller than the pN- to nN-scale forces that are required to induce conventional 'mechanosensitive' signaling through integrins (Matthews et al., 2006; Overby et al., 1 Acta Biomaterialia, 295-303 (2005)), or stress-sensitive ion channels (Sukharev et al., 113 J. Gen. Physiol. 525-40 (1999). In contrast, application of similar magnetic fields to cells treated with DNP-coated nanobeads that lacked bound IgE, or to IgE-presenting cells pre-treated with uncoated nanobeads, consistently failed to induce a calcium response (FIG. 7). Thus, activation of calcium signal transduction is not due to needle placement, heat generation or other nonspecific effects that can occur with use of extremely low-frequency magnetic fields (McCreary et al., 27 Bioelectromagn. 354-64 (2006)); rather, it depends directly on the intensity and distribution of the applied magnetic field, which magnetizes the receptor-bound superparamagnetic nanoparticles.

Microfluorimetry also revealed that calcium levels decrease within seconds of attenuating the magnetic pulse, and that calcium waves can be repeatedly induced in the same cells by re-administering magnetic pulses (at 1 Amp) (FIGS. 4A, 4B; see also Mannix et al., 3 Nature Nanotechnology 36-40 (2008), Published online: Dec. 23, 2007, Movie 1). Even tighter coupling between stimulus and response was obtained by sequentially stimulating the cells with 40-s magnetic pulses separated by 20-s rest periods. This resulted in an oscillating pattern of multiple calcium waves with a frequency response that closely matched that of the electromagnetic stimulus, both within whole populations (FIG. 4C) and in individual cells (FIGS. 4B, 4D), although gradual accumulation of intracellular calcium was observed in most cells. Thus, magnetic fields can be used to selectively activate a rapid calcium signaling response and to produce controlled calcium oscillations by harnessing natural transmembrane receptor signaling mechanisms in living cells.

Hence, an embodiment of the present invention provides a nanomagnetic cellular switch by conjugating paramagnetic nanobeads, such as superparamagnetic nanobeads, to ligands. For example, single anti-integrin Fab fragments or RGD peptides or the like may be used. When these beads bind to cell surface integrin receptors in the absence of an applied field, they ligate individual receptors without promoting receptor oligomerization. In contrast, when a magnetic field is applied, magnetization of the beads results in their agglomeration and associated receptor clustering, thereby switching on the cAMP signaling response. Similar activation of protein tyrosine phosphorylation cascades can be accomplished by magnetically clustering cytokine receptors, such as receptors for epidermal growth factor (EGF) or platelet derived growth factor (PDGF). A similar approach may be used with any receptor or other cellular molecule that requires oligomerization for activation, including G protein and inositol lipid signaling.

This and other embodiments of the present invention capitalize upon other methods for pharmacologically regulated cell therapy using receptor clustering-mediated signal transduction to initiate a signal for proliferation or differentiation. Other approaches have proposed biochemical ligand signaling on of a population of genetically modified cells. See, for example, WO 99/34836, U.S. Pat. No. 5,741,899, U.S. Pat. No. 5,359,046, U.S. Pat. No. 5,869,337, U.S. Pat. No. 6,046,047, U.S. Pat. No. 5,994,313; and Neff & Blau, Blood, 2535-40, (2001).

The ligands of the present invention are capable of being distributed on a one-ligand-per-nanoparticle basis. These may include an antibody, a monoclonal antibody, Fab antibody fragment or a single specificity antibody, which may be human, humanized, chimeric, or in vitro generated. The term "antibody" also includes immunoglobulin, and includes any portion of an antibody obtained from any technology known in the art that binds to the particular target epitope of interest, such as a receptor.

The ligand may also be all or portion of the natural ligand for a given receptor. See, e.g., U.S. Pat. No. 5,741,899 and U.S. Pat. No. 5,994,313. The ligand may also be chemical in nature, such as chromium salt, or any monovalent artificial ligand that may be created for a particular target. For example, the monovalent synthetic ligands that bind immunophilin molecule receptors such as FKBP binding domain, as described in U.S. Pat. No. 6,150,527 and in U.S. Patent application publication No. 20050238628.

The ligand may also be, or include, synthetic peptides, nucleotides, carbohydrates, lipids, or polymers composed of these molecules.

Intracellular signal transduction is also often mediated by binding or clustering of two or more specific molecules in the cytoplasm, nucleus, or other intracellular compartments that only trigger downstream signaling and biochemical responses when one or more of these molecules are post-translationally modified, such as by protein phosphorylation, myristoylation or binding to calcium, cAMP or di- or tri-nucleotides, and thereby induced to close physical apposition within multimolecular complexes or clusters. Examples include transcription fingers via zinc finger domains, ryanodine receptors and specific cAMP binding domains, such as the KID and KIX domains of CREB and CREB-binding protein. Hence, in another embodiment, the systems and methods of the present invention provide for the activation of intracellular biochemical responses by introducing magnetic nanoparticles into the cytoplasm, nucleus, or other intracellular compartments that bind to two or more molecules without activating these molecules, and then being able to cluster these components by applying magnetic fields. Many techniques for such introduction are well-known in the art, such as proteofection, electroporation, microinjection, etc. When bound to the target molecules and then magnetized, the magnetic particle-bound molecules attract each other and force the molecules to dimerize or cluster. This magnetic force-induced molecular aggregate triggers the desired biochemical events inside the cell. In this fashion, the present invention employs magnetic forces to physically promote molecular aggregation and thereby mimic clustering-dependent activation mechanisms that are induced by specific binding of different molecules through chemical modifications that mediate signal transduction.

For example, regarding manipulation of cellular nuclear functions, "zinc fingers" are proteins that recognize a specific three base pair sequence of DNA, and are of great interest to researchers working in the field of gene therapy. Their potential uses range from conferring DNA binding to chimeric nucleases, to creating artificial transcription factors. See Dove et al., 386 Nature 627-30 (1997). Zinc fingers proteins have tails that bind avidly when appropriately modified through post-translational modification in living cells, and these binding domains may be removed and bound to the paramagnetic particle. Magnetic activation then effects zinc finger dimerization, allowing manipulation of target transcription factors and target gene expression.

Another example embodiment allows the manipulation of the kinase inducible domain (KID) of CREB and the KIX domain of CREB-binding protein. These proteins may be genetically engineered proteins that contain these domains that normally bind when cAMP goes up in the cells and this brings whatever proteins that are individually connected to either KID or KIX peptide sequences together into a cluster, but only when cAMP is present. A model for this approach employed magnetic cellular switches with two halves of beta-lactamase using 'protein fragment complementation'. When cAMP is present these two domains bind to each other pulling the halves of the BLA they are each linked to together thereby restoring BLA enzyme activity and producing signal output (Overby et al., 40(4) IEEE Transaction Magnetics, 2958-60 (2004)). In the present embodiment, those halves of BLA are bound with magnetic nanoparticles, and then magnets, rather than cAMP, are then used to accomplish the association of the domains. This approach may be used with any two molecules that normally do not bind unless in the presence of a particular 'signal' that changes molecular conformation (e.g., cAMP, calcium, phosphorylation, etc.), or the normal associating signal may be bypassed by using magnetic forces to cluster the molecules closely.

This approach may also be modified and adapted for use in a wide variety of recombinant expression scenarios to switch on and switch off the expression of a particular protein or cellular behavior. Cells may be genetically engineered to act as cellular 'devices' using synthetic biology or genetic engineering to express a drug, for example, insulin, and be sensitive to a signaling pathway that could be activated by magnetically clustering particular receptors on those cells. These cells might be systemic or placed in skin and easily controlled by a magnetic 'wrist watch' type device.

A micro-scale version related to the present invention was used to promote membrane receptor clustering in RBL-2H3 mast cells. See Mannix et al., 3 Nature Nanotech. 36-40 (2008). Magnetic nanoparticles (30-nm) were coated with one dinitrophenol-lysine ligand each and bound to cell surface IgE-FcϵRI receptor complexes. An electromagnetic micro-needle actuator that applies a magnetic field (Matthews et al., 85 Appl. Phys. Lett. 2968-70 (2004)), was positioned so that the field vector was at a small angle to the plane of the cell layer. Activating the field in the needle magnetized the magnetic nanoparticles, thereby inducing a receptor clustering in cells within the culture as the particles pulled on neighboring magnetized particles like closely apposed bar magnets. The receptor clustering resulted in the activation of cluster-mediated intracellular calcium signaling. An aspect of this embodiment may be used as a biosensor; another as an actuator of cellular behaviors, including secretion, contraction, electrical signaling and gene expression.

Moreover, the precision with which the present invention manipulates calcium channels provides the ability to control not only calcium pathway-related cell functions, but provides a mechanism by which any cell that uses calcium to regulate its activity may be controlled by the systems and methods provided herein.

Most of the nanomagnetic particles used in previous studies were made from iron oxides, such as magnetite ($Fe_3O_4$) and maghaemite ($\gamma Fe_2O_3$), although some larger (4 μm) CrO2 particles have been used in magnetic twisting cytometry and tissue engineering applications. In particular applications, magnetic cores may be coated with biocompatible polymers, such as polyvinyl alcohol, silica and dextran that bind readily to biomolecules or specific antibodies. See, e.g., Berry & Curtis, 36 J. Phys. D, R198 R206 (2003). Iron oxides are also endogenous in the human body and similar to materials used as magnetic resonance imaging contrast agents. As such, they are usually well tolerated by cells. For in vivo applications, however, toxicity must be evaluated thoroughly. See Neuberger et al., 293 J. Magn. Mater. 483-496 (2005).

The nanomagnetic particles of the present invention may be paramagnetic or superparamagnetic. Paramagnetism occurs only in the presence of an externally applied magnetic field. Unlike ferromagnets, paramagnets do not retain any magnetization in the absence of an externally applied magnetic field. Thus, the total magnetization will drop to zero when the applied field is removed. Superparamagnetism relates to the energy required to actuate and demagnetize a paramagnetic material. Nanomagnetic particles (5 nm to 500 nm; superparamagnetic) are commercially available from, for example, Miltenyi Biotec (Auburn, Calif.). As with micro- or ferromagnetic particles, the paramagnetic nanobeads of the present invention may be coated with biocompatible polymers, such as polyvinyl alcohol, silica, and dextran that bind readily to ligands such as synthetic peptides or antibodies.

Further regarding t magnetic particles, the size of the magnetic particles used in current technology ranges from a few to several hundred nanometers. Generally, smaller particles (30 nm) are used in studies that target specific molecules on the cell membrane or in the cytoplasm or nucleus. As iron oxide nanoparticles become superparamagnetic below about 30 nm, larger particles must contain multiple smaller nanoscale paramagnetic crystal components. The superparamagnetic particles of present embodiments may range in size from about 5 nm to about 500 nm.

In an alternative embodiment of the present invention, paramagnetic nanoparticles are introduced into the cytoplasm, nucleus, or other intracellular compartments of the cell. This can be accomplished using proteofection methods, such as particles coated with TAT-containing peptides, or by electroporation or microinjection.

In additional biomedical applications, current magnetodynamic therapy (MDT) harnesses Magnetic Resonance Imaging (MRI) techniques with engineered enhanced ferrites as the MRI contrast agent. In this approach, if a tumor is detected, the practitioner increases the power to the MRI coils, and localized heating destroys the tumor region without damage to the surrounding healthy cells. Another promising MDT employs magnetic nanoparticles that are coupled to the radio frequency of the MRI. This coupling converts the radio frequency energy into heat energy that kills the cancer cells. Additionally, nanoparticles are able to target tumor cells. Because the nanoparticles target tumor cells and are substantially smaller than human cells, only the very few tumor cells next to the nanoparticles are killed by application of more intense MRI radio signals, which greatly minimizes damage to healthy cells. Current approaches differ from the present invention in that they use ferromagnetic nanoparticles as opposed to paramagnetic or superparamagnetic nanoparticles, and they use magnetic fields to produce heating through these particles. The present invention uses magnetic fields to magnetize the particles and thereby induce their aggregation.

Magnetic field strengths may be generated by electromagnets, including Helmholtz coils, Magnetic Resonance Imaging, and the like. Field strengths ranging from 0.001 Tesla (T) to 10 T have been used for the clustering/switching of superparamagnetic nanoparticles from 5-100 nm in diameter. Penetration depths of 5 cm and more may be achieved based on the particle size and the field strength used.

For example, a low field strength of 0.05 Tesla (T) induces clustering of 5-20 nm diameter magnetic nanoparticles. Field strengths of this magnitude may be generated with electromagnets or with Helmholtz coils, including Helmholtz coils with B~350,000 T pulses. Additionally, MRI systems typically used in hospitals and other clinical environments generate sustained magnetic field strengths of 0.15-3.0 T and allow for significant penetration depths of 5 cm and more. Further, many MRI systems include superconducting magnets having a magnetic field strength of 14 T or more. These MRI systems may be utilized for whole body imaging with ~30 nm magnetic nanoparticles and will have even greater penetration depths (greater than 5 cm).

The embodiments of the present invention are well suited for clinical use. For example, in patients suffering melanoma or other skin cancers, or in cosmetic and dermatological applications, such as in the removal of warts, spider angiomata, or other surface skin lesions, paramagnetic nanoparticles may be injected directly into the lesion, or in an upstream blood vessel. These paramagnetic nanoparticles may be associated with monovalent portions of FasL, TNF-α, or TRAIL ligands, and introduced into the patient where they occupy, but do not cluster, the respective Fas, TNFR1, and DR5 "death receptors." Local application of the magnetic field, focusing a high magnetic field only on the lesion to be removed, will only induce particle aggregation, receptor clustering and cell death signaling in these locations. The magnetic field is held relatively static by applying the magnetic field against the skin or only to the portion of the body exhibiting the lesion. Upon application of the magnetic field, the "death receptors" cluster and initiate the apoptosis cascade. In this embodiment, the magnet can be a stationary magnet directly in contact (pressed tightly to) with the lesion, or may be a tapered magnetic needle as discussed herein, or an electromagnet. Stationary magnets may be comprised of samarium cobalt or neodymium iron boron, for example, or other rare earth magnets. Alternatively, any electromagnetic configuration with an appropriate pole tip configuration to target the intensity fields to the proper location may be used to deliver the magnetic field. This approach takes advantage of the natural apoptosis signal without the need for introduction of genetically modified cells bearing the suicide switch. Alternatively, paramagnetic nanoparticles are associated with a portion of an intracellular adapter molecule such as FADD or TRADD, or with a portion of the procaspase-8 complex, and are introduced into the cell. Upon application of the localized magnetic field, the active caspase-8 cluster forms and thereby triggers apoptosis by activating caspase-3, -6, and -7. Importantly, even if the monovalent magnetic particles travel to other parts of the body they will not produce toxicity as long as the magnetic field is not present in those regions and is only limited to the lesion of interest.

In instances where lesions exist deeper within the tissue, nanoparticles may be either injected systemically or injected near or into the site of the lesion. If desired, the nanoparticles might be delivered within a sustained-release excipient, which are well-known in the art, such as a hydrogel, to deliver the nanoparticles over time. The nanoparticles may then be actuated by insertion of a fine long electromagnetic needle transdermally, much like when surgeons inject long needles into the liver, bone marrow or brain to obtain biopsies or cerebral spinal fluid. See, e.g., WO2006039675. The surface of the needle may be modified to produced enhanced magnetic field gradient configurations. A similar approach is applicable to prostate cancer, where the magnetic field is applied via a rectal probe. Alternatively, stronger magnetic fields may applied non-invasively.

In contrast to apoptosis, embodiments of the present invention also may be used to provide cell or tissue growth. For example, many growth factor receptors, such as platelet derived growth factor (PDGF) and epidermal growth factor (EGF) receptors may be clustered by the system and method of the present invention. As a particular example, erythropoietin (Epo) has been used in cancer patients suffering from anemia. Epo treatment has recently been shown to be problematic, however, as Epo may enhance the growth of particular tumors. A system and method of the present invention provides an alterative approach, whereby EpoR may be activated without systemic administration of Epo, by administering EpoR ligands (Epobp or antibodies against EpoR) bound to paramagnetic nanoparticles, such that applying a magnetic field clusters EpoR in the bone marrow where erythrocyte production is desired, and not at the primary tumor site. This also may be carried out with or without additionally triggering clustering of EpoR with JAK2. Additionally, localized Epo has been reported to protect ischemic myocardium. Currently, however, the effective dose of Epo is too high to administer clinically. By applying a magnetic field in the area of the heart, Epo's effect could be mimicked locally and the heart protected from further pathology.

Similarly, thrombopoietin (Tpo) acts through its receptor, Mpl, to stimulate the proliferation and maturation of megakaryocytes and their progenitors. Mpl contains various docking sites, any one of which might be filled by the appropriate ligand-paramagnetic nanoparticle. In this way, application of the magnetic field causes the clustering and activation of Mpl- and stimulates megakaryocyte growth. Because the megakaryocyte is a bone marrow cell responsible for the production of blood platelets necessary for normal blood clotting, those suffering from clotting disorders might benefit from this approach.

Aside from cell growth, other stimulatory functions may be actuated. For example, one might activate integrin on platelets using a magnetic "wand" to induce clot formation where it is needed. Similarly, stronger magnetic fields may be employed to stop internal bleeding.

As a further example, gamma-amino butyric acid (GABA) acts as a major inhibitory neurotransmitter in the central nervous system. When the level of GABA in the brain decreases below a certain level, seizures and other neurological disorders may occur. Most GABA found in the brain is manufactured there, because GABA is not transported efficiently into the brain from the bloodstream. The $GABA_A$ and $GABA_C$ receptors are ligand-gated ion channels that may be bound by ligand-associated paramagnetic nanoparticles then clustered by magnetic field to mimic authentic GABA-induced activity.

Other example receptors, known to cluster for activation, that may be useful according to the present invention include, but are not limited to: Neurotransmitters such as acetylcholine receptor, Glycine receptor, glutamate receptor, GABA receptor; Growth Factors such as EGF receptor; Immunologic receptors such as T cell receptor, Fc receptors, CD59 receptor, CD2; Metabolic receptors such as low density lipoprotein receptor, alpha-amino-3-hydroxy-5-methylisoxazole-4-propionic acid receptor; Urokinase receptor; Insulin receptor; C3Bi receptor; Integrin Receptor; Fibrinogen receptor; Fas receptor; Thyrotropin receptor; Bacterial chemotaxis receptors; and Yeast Pheromone receptor.

The cells of the present invention may be controlled in vitro, in vivo, or ex vivo. Example cells that may be controlled include nerve, muscle, epithelial, endothelial, connective tissue, blood or inflammatory cells, such as cancer cells, dendritic cells, nerve cells, muscle cells, heart cells, eye cells, and ear cells.

Manipulation of nanoscale magnetic particles may be carried out using specialized magnet architectures to create higher field gradients. For example, femtosecond lasers may optically etch the surfaces of magnetizable materials, such as "surgical" carbon steel and cobalt-coated silicon. This approach has been used to microfabricate surface architectures containing topographical features with high curvature in the nanometer to low micrometer range that locally concentrate magnetic field gradients with high efficiency. More effective magnetic gradient concentrators may be used to magnetically activate signal transduction in conjunction with receptor-bound nanobeads on the cell surface. This might be integrated into microfluidic systems and other systems that employ cell-based biochips.

Future treatment of diseases or conditions based on the remote manipulation of receptor-mediated signal transduction within specific organs and tissues may be possible.

EXAMPLES

Example 1

Nanomagentic Control of Mast Cell Receptor Signal Transduction Cell Culture

Rat basophilic leukaemia RBL-2H3 mast cells (American Type Culture Collection, Manassas, Va.) were cultured in Dulbecco's modified Eagle's medium (DMEM) supplemented with 10 mM N-2-hydroxyethylpiperazine-N-2-ethanesulphonic acid (Hepes), 2 mM L-glutamine, 100 U $ml^{-1}$ penicillin, 100 μg $ml^{-1}$ streptomycin and 10% fetal bovine serum (Invitrogen) at 37° C. under 5% $CO_2$. For calcium ratiometric imaging, cells were seeded sparsely on coverglass-bottomed 35-mm dishes (MatTek) and cultured for 24 h. Mouse monoclonal anti-DNP IgE antibodies (Clone SPE-7, Sigma-Aldrich) were added (63 μg $ml^{-1}$) and cells were cultured overnight. Cells were then washed twice with DMEM supplemented with 1% bovine serum albumin (Intergen; Cohn fraction V) and 20 mM Hepes buffer, pH7.4 (DMEM-BSA) to remove unbound IgE antibodies and serum components. The magnetic nanobeads were then added to the cells ($1.25 \times 10^{13}$ nanobeads $ml^{-1}$) with 10 μM Fura2-AM in DMEM-BSA for 3 h at 37° C. Cells were washed free of non-adherent nanobeads and excess Fura2-AM before analysis by multiple washes in DMEM-BSA and Hank's Balanced Salt Solution supplemented with 1% BSA and 20 mM Hepes, pH 7.4. The washed cells were transferred into microscope analysis medium that maintains a stable pH under room air composed of Hank's salts-based Minimum Essential Medium (MEM; minus MEM vitamins and phenol red), 2 mM L-glutamine, 1 mM sodium pyruvate, 1% BSA, 10 µg ml$^{-1}$ high-density lipoprotein (Bionetics Research), 5 µg ml$^{-1}$ holo-transferrin (Collaborative Research) and 2 mM Hepes, pH 7.4.

Imaging

Cytosolic calcium levels were quantified using microfluorimetry in cells cultured on an automated stage (LUDL Electronics Products) of a Nikon Diaphot 300 inverted microscope (Nikon USA) fitted with a quartz×20 objective (0.5 NA) and a Polychrome II high-speed 75 W xenon lamp monochromator (TILL Photonics LLC) that illuminates cells with alternating 340 nm and 380 nm light for Fura2-AM dye excitation. The stage was heated to 37° C. using a custom-built stage heater (MVI) fitted with an Omega CN9000A heat controller (Omega Engineering). Emission fluorescence at 510 nm±40 nm was captured by an Orca 100 CCD 12-bit digital camera (Hamamatsu, Japan) with 4×4 pixel binning. Fura2-AM ratio images (340/380 nm) were produced at 20 s intervals between image pairs using image background subtraction and noise reduction functions of IPLab Ratio software (Scanalytics, BD Biosciences). Ratio images were converted into calcium concentrations based upon a standard curve generated in RBL-2H3 cells treated with 10 µM ionomycin at 37° C. in the presence of various calcium concentrations in 150 mM KCl buffer (Grynkiewicz et al., 260 J. Biol. Chem. 3440-50 (1985)); the Kd of Fura-2 binding to calcium was determined to be 22 nM in these cells.

For scanning electron microscopy studies, 2.5% glutaraldehyde was added to cells pre-incubated with IgE and monovalent DNP beads either before or after exposure to an electromagnetic pulse (1A) for 1 min, and the magnetic field was maintained for an additional minute. Cells were post-fixed with 1% osmium tetroxide, sputter-coated with gold (4 nm), and images recorded using a Leo 982 field emission scanning electron microscope (LEO Electron Microscopy).

Magnetic Nanobeads

Superparamagnetic nanobeads (30 nm diameter, 5 nm iron core) coated with 30 amine groups per bead by the manufacturer (Nanocs) were placed in an ultrasonic bath for 10 s at room temperature to ensure a single bead suspension before being coated at different ratios (0:30, 1:29, 3:27 and 30:0) of Nε-2,4-dinitrophenyl-L-lysine (DNP-lysine):L-lysine (Sigma-Aldrich) to vary the average number of DNP ligands per bead. The nanobeads were washed four times with 0.1M 2-[N-morpholino]ethanesulphonic acid pH6.3 buffer (MES buffer) and treated with 5% glutaraldehyde (Electron Microscopy Sciences) for 3 h at 25° C. in the same buffer to activate the surface amines. Beads were then washed, collected using MACS MS reversible magnetic steel wool columns (Miltenyi Biotec) and incubated (12 h, 4° C.) with a total of 100 µg of DNP- and L-lysine in 500 µl MES buffer. The reaction was quenched by adding 100 µl of 1 M ethanolamine (pH 8) and incubating for 1 h at 25° C. See Song et al., 14 J. Mater. Chem. 2643-48 (2004). The nanobeads were then collected in 500 µl distilled water, and 34 µl of x 10 phosphate buffered saline (without calcium or magnesium) was added to produce a slightly hypotonic solution to prevent nanobead aggregation. The coated beads were sonicated in a bath for 10 s at room temperature before being added to cells. Bead aggregation was not observed when DNP beads were used at dilutions of 1:4 or higher in culture medium.

Magnetic Control of Calcium Signaling

Magnetic DNP beads adherent to cell surface FIERI receptors through bound anti-DNP IgE antibodies were magnetized using a water-cooled, temperature-controlled electromagnetic microneedle (Matthews et al., 119 J. Cell Sci. 508-18 (2006)), containing a 20-µm-diameter pole tip (Matthews et al., 85 Appl. Phys. Lett. 2968-70 (2004)). The electromagnetic needle was precisely positioned within the culture dish using an automated Micromanipulator (Eppendorf AG) so that the needle tip was visible within the high-power optical field, approximately 30 µm above the cell surface, at an angle of 45°, and not touching any cells. The magnetic field was controlled by manually switching the electric current supplied to the electromagnetic needle during ratio image capture using a regulated DC power supply (Summit Co., Korea).

The spatial decay of the microneedle's magnetic fields was calculated using finite element analysis. A 1 µm-thick cross-section of a microneedle with a 20 µm-diameter tip was input into Finite Element Method Magnetics (FEMM) software (D. C. Meeker, Version 4.0.1). The calculated fields were scaled by a constant so that calculated forces would conform to previously published calibration studies which used the microneedle to pull 4.5 µm-diameter beads through solutions of defined viscosity in the same experimental system (Overby et al., 1 Acta Biomater. 295-303 (2005)). Forces were then calculated using the expression $F=(m(x)\nabla)B(x)$, where m is the estimated magnetization of the bead, B is the calculated field, and x is the needle position. For this scaling, the distance between the microbeads and the needle was set to be greater than three times the bead diameter, consistent with experimental conditions in which the needle was held >30 µm from the cell surface. Bead magnetization was assumed to be linear with respect to the magnetic field below a saturation field of 0.1 T. The fields were scaled to forces assuming an electromagnet current of 250 mA. All calculations other than the finite element analysis were performed using Matlab (Mathworks, Natick, Mass.).

The magnetic force exerted by the microneedle on an individual nanobead was calculated according to the equation $F=(m(x)\nabla)B(x)$. The saturation magnetization of the nanobeads was calculated assuming that the bead's 5 nm iron core has a magnetization per unit volume equal to that of Dynal 2.8 µm-diameter beads (Invitrogen), which are 12% iron by volume per manufacturer's specifications. The magnetization was assumed to be linear below the saturation field of 0.1 T; the microneedle was assumed to be positioned at a 45° angle to the horizontal; and the nanobeads were assumed to lie in a horizontal plane 30 µm below the microneedle tip. Forces were separated into components tangential and normal to the plane. Forces between magnetic nanobeads were estimated using an analytic equation expressing the force between two point-dipoles as a function of the distance between them (Yung et al., 9 Magn. Electr. Sep. 39-52 (1998)). Nanobeads were assumed to be separated from each other by an average distance of 30 nm, which is based on experimental measures of SEM images of multiple cells. Forces were separated into components tangential and normal to the plane.

Figure 6:
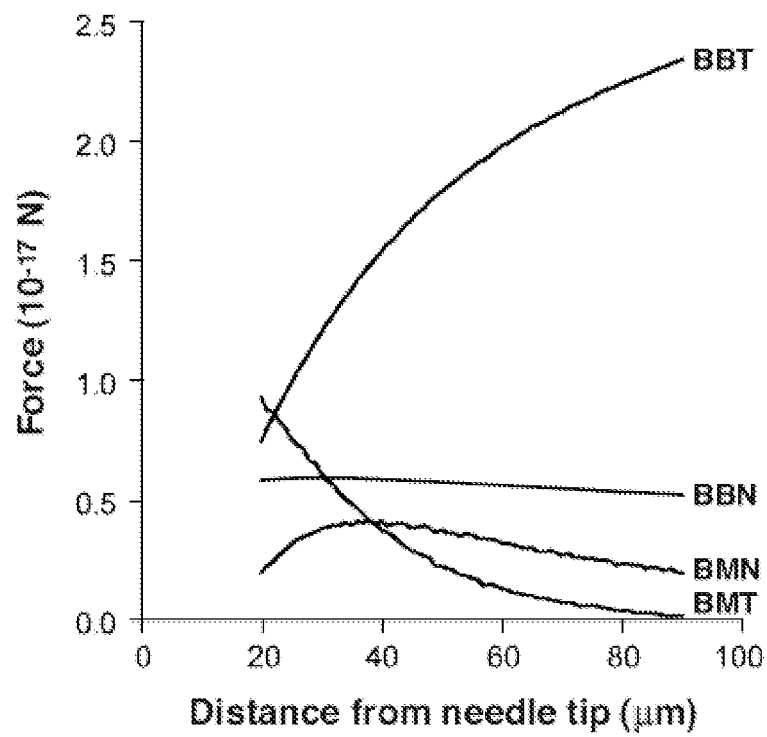
FIG. 6. Finite element modeling of magnetic forces experienced by surface receptor-bound nanobeads. Finite element modeling of the interactions between the magnetic microneedle and nanobeads yields the bead-bead normal (BBN) and tangential (BBT) forces between the adjacent nanobeads, and the normal (BMN) and tangential (BMT) forces between the magnetic microneedle and a given bead as a function of separation distance between the microneedle and the cell surface. For all separation distances greater than ~22 µm, tangential attractive forces between the nanobeads dominate all other forces (a distance of ~30 µm was used in this study).

Using this model, the magnitudes of forces between the magnet and beads, and between neighboring beads, in both the normal and tangential directions were calculated. (FIG. 6). For all microneedle-bead separation distances greater than ~22 µm, the magnitude of the tangential attractive force between neighboring beads is nearly an order of magnitude larger than either the normal or tangential force between the microneedle and the beads (this distance was >30 µm in the present study). Moreover, the magnitude of the normal (tensional) force on the beads is less than $10^{-17}$ µmN, several orders of magnitude smaller than the pN- to nN-scale forces previously found to be required to induce "mechanosensitive" signaling pathways through integrins bound to 4.5 µm-diameter beads using this experimental system (Overby et al., 2005; Matthews et al., 2006) and others have found to be required to activate stress-sensitive ion channels (Sukarhev et al., 113 J. Gen. Phys. 525-40 (1999)).

What is claimed is:

1. A method of nanomagnetic actuation of receptor-mediated signal transduction to control cellular behavior, the method comprising:
adding monovalent paramagnetic nanoparticles to living cells to occupy cell surface receptors without activating the receptor, thereby creating bound nanoparticle-receptor complexes;
applying a magnetic field to magnetize the paramagnetic nanoparticles in the nanoparticle-receptor complexes and to induce cohesion of the bound nanoparticle-receptor complexes;
wherein said cohesion aggregates the bound nanoparticle-receptor complexes on a membrane of the living cells to produce receptor clusters that activate intracellular signaling responses only while the magnetic field is applied.

2. The method of claim 1, wherein the paramagnetic nanoparticles have a diameter ranging from about 5 nm to about 500 nm.

3. The method of claim 2, wherein the paramagnetic nanoparticles are superparamagnetic nanoparticles.

4. The method of claim 1, wherein the initial occupation of the receptor by the nanoparticle is achieved by conjugating each paramagnetic nanoparticle to at least one ligand.

5. The method of claim 1, wherein the activated receptor activates changes in cellular biochemistry at the membrane, or in the cytoplasm, nucleus or other intracellular organelles.

6. The method of claim 1, wherein the activated receptor activates calcium signaling in the cell.

7. The method of claim 1, in which the cells are selected from the group consisting of nerve, muscle, heart, epithelial, endothelial, connective tissue, blood or immune cells.

8. A nanomagnetic actuation system to induce receptor-mediated signal transduction to control cellular behavior, the system comprising:
at least one isolated cell;
individual monovalent nanoparticle-receptor complexes comprising paramagnetic nanoparticles bound to cell surface receptors; and
a magnetic field applicator adapted to sufficiently magnetize the paramagnetic nanoparticles in the nanoparticle-receptor complexes to induce clustering of the bound nanoparticle-receptor complexes;
whereby upon exposure to said magnetic field effective to induce clustering of said receptors, signaling responses that control intracellular biochemistry and behavior are activated only while the magnetic field is applied.

9. The system of claim 8, wherein the paramagnetic nanoparticles have a diameter ranging from about 5 nm to about 500 nm.

10. The system of claim 8, wherein the paramagnetic nanoparticles are superparamagnetic nanoparticles.

11. The system of claim 8, wherein the initial binding of the receptor by the nanoparticle is achieved by conjugating each paramagnetic nanoparticle to at least one ligand.

12. The system of claim 8, wherein the activated receptor activates changes in cellular biochemistry at the membrane or in the cytoplasm, nucleus or other intracellular organelles.

13. The system of claim 8, wherein the activated receptor activates calcium signaling in the cell.

14. The system of claim 8, in which the cell is selected from the group consisting of nerve, muscle, heart, epithelial, endothelial, connective tissue, blood or inflammatory cells.

15. The system of claim 8, wherein the magnetic field applicator includes an electromagnet.

16. The system of claim 8, wherein the magnetic field applicator includes a permanent magnet.

17. The system of claim 8, wherein the magnetic field applicator includes a control module adapted to periodically apply the magnetic field.

18. The system of claim 8, wherein the bound nanoparticle-receptor clusters activate intracellular signaling responses and further generate the receptor signals.

19. The system of claim 8, further comprising a non-invasive detector selected from the group consisting of an optical detector, a microelectronic sensor, a chemical sensor, and a magnetic resonance imager.

20. The system of claim 8, wherein the magnetic field applicator generates a high density multiplexed magnetic field gradient.

21. The system of claim 8, wherein the nanomagnetic particles are coated with at least one non-aggregating receptor ligand.

22. The system of claim 21, wherein said ligand is an antibody or a portion of an antibody, a peptide, a nucleotide, a carbohydrate, a lipid, or polymer of these.

* * * * *